(12) United States Patent
Garrison et al.

(10) Patent No.: US 9,693,789 B2
(45) Date of Patent: Jul. 4, 2017

(54) SYSTEMS AND METHODS FOR ASPIRATING FROM A BODY LUMEN

(71) Applicant: Silk Road Medical, Inc., Sunnyvale, CA (US)

(72) Inventors: Michi E. Garrison, Sunnyvale, CA (US); Sieu Duong, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 418 days.

(21) Appl. No.: 14/221,917

(22) Filed: Mar. 21, 2014

(65) Prior Publication Data

US 2014/0296868 A1 Oct. 2, 2014

Related U.S. Application Data

(60) Provisional application No. 61/806,707, filed on Mar. 29, 2013.

(51) Int. Cl.
*A61B 17/22* (2006.01)

(52) U.S. Cl.
CPC .... *A61B 17/22* (2013.01); *A61B 2017/22079* (2013.01)

(58) Field of Classification Search
CPC ..................................................... A61B 17/22
See application file for complete search history.

(56) References Cited

U.S. PATENT DOCUMENTS

| | | |
|---|---|---|
| 3,709,461 A | 1/1973 | Johnson |
| 3,819,091 A | 6/1974 | Hollender |
| 3,939,835 A | 2/1976 | Bridgman |
| 4,036,232 A | 7/1977 | Genese |
| 4,594,073 A | 6/1986 | Stine |
| 4,711,250 A | 12/1987 | Gilbaugh, Jr. et al. |
| 4,850,979 A | 7/1989 | Swallert |
| 4,998,915 A | 3/1991 | Hannah |
| 5,115,816 A | 5/1992 | Lee |
| 5,469,860 A | 11/1995 | De Santis |
| 5,830,152 A | 11/1998 | Tao |
| 6,158,467 A | 12/2000 | Loo |
| 6,413,235 B1 | 7/2002 | Parodi |
| 6,423,032 B2 | 7/2002 | Parodi |
| 6,595,953 B1 | 7/2003 | Coppi et al. |
| 6,837,881 B1 | 1/2005 | Barbut |
| 7,083,594 B2 | 8/2006 | Coppi |
| 7,470,249 B2 | 12/2008 | Junger |
| 7,879,012 B2 | 2/2011 | Kane et al. |
| 8,191,457 B2 | 6/2012 | Kanner et al. |
| 2005/0154349 A1 | 7/2005 | Renz et al. |

OTHER PUBLICATIONS

Henry et al. (1999) "Carotid Stenting With Cerebral Protection: First Clinical Experience Using the PercuSurge GuardWire System" J. Endovasc. Surg. 6:321-331.

*Primary Examiner* — Leslie Deak
*Assistant Examiner* — Kai Weng
(74) *Attorney, Agent, or Firm* — Mintz Levin Cohn Ferris Glovsky and Popeo, P.C.

(57) ABSTRACT

An aspiration device can be used to aspirate an obstruction from a blood vessel. The aspiration device is configured to allow controlled one-handed aspiration yet maintain a syringe plunger feel of vacuum. The aspiration device also allows one-handed injection to empty the device when needed. Furthermore, mechanisms enable one-handed locking of a plunger position of the device to maintain vacuum when the user releases the device.

6 Claims, 20 Drawing Sheets

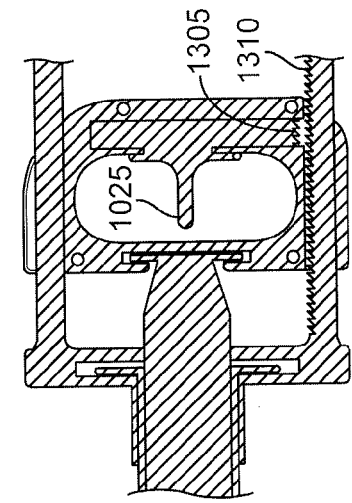
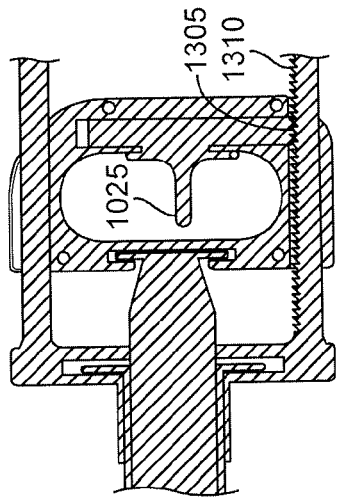
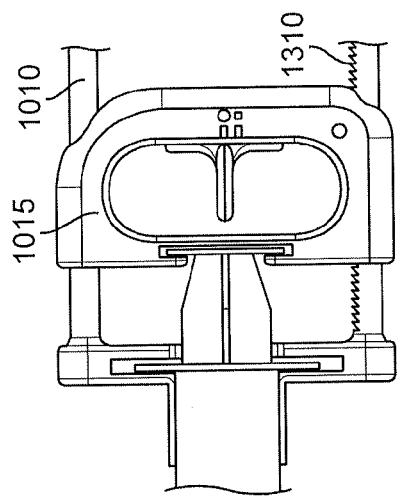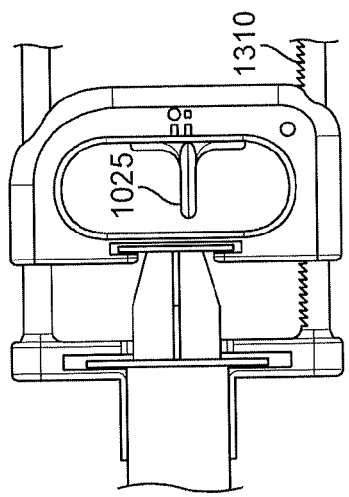
FIG. 12
FIG. 13

SYSTEMS AND METHODS FOR ASPIRATING FROM A BODY LUMEN

REFERENCE TO PRIORITY DOCUMENT

This application claims priority to U.S. Provisional Patent Application Ser. No. 61/806,707 filed Mar. 29, 2013. Priority to the aforementioned filing date is claimed and the disclosure of the provisional patent application is incorporated herein by reference in its entirety.

BACKGROUND

Aspiration has been used as a method to remove thrombotic blockages from blood vessels. For example, a single lumen catheter is sometimes used to aspirate a clot from a cerebral vessel in an acute ischemic stroke patient. Such a procedure generally entails placing a distal tip of a catheter at the proximal face of the clot and applying vacuum to the clot via a proximal port of the catheter. The clot may be soft enough to be aspirated into the catheter, or in cases of harder clots aspiration on the catheter attaches the clot to the distal tip of the catheter and the attached clot removed together with the catheter. In some cases, the clot is broken up by mechanical means during aspiration, to aid in aspiration of the clot through the catheter.

The aspiration source may be a suction pump or simply a syringe, each of which has pros and cons. An advantage of a syringe is that a syringe can generate near full vacuum by the user pulling back forcefully on the syringe plunger to generate a strong force. This force is somewhat independent of the size of the syringe, in that even a small syringe can generate near full vacuum. A larger syringe size simply allows a greater amount of fluid and/or clot to be aspirated during one "pull back".

The syringe also allows the user to "feel" if the distal end of the catheter is blocked by the tactile feedback of a counter force on the plunger of the syringe. The syringe also allows the user to easily vary the force and/or rate of suction. However, there are also some disadvantages of a syringe. A syringe is designed for controlled one-handed injection into the vessel, which is not optimally designed for one-handed pull back or aspiration from the vessel. To maintain a full vacuum requires constant manual hold on the syringe barrel and plunger, which can be cumbersome. If the user wishes to let go of the syringe momentarily, the vacuum may be lost. A locking syringe may be used to counter this by permitting the user to lock the syringe in a vacuum state. But such locking syringes require two hands to lock, and usually only lock in discrete positions. Moreover, locking the syringe in full pull-back would remove the "feel" of the syringe plunger. In addition, once a syringe is filled, it needs to be removed, emptied, and reattached to the catheter if further aspiration is desired. These extra steps require a pause in the procedure, a loss of vacuum when the syringe is detached unless a stopcock is used, and two hands to remove the syringe.

In contrast, the suction pump is advantageous in that it is "hands free" and has unlimited length of time for suction without the need to pause, as compared to a syringe. However, there are limitations to the suction pump. First, there is limited aspiration force as compared to a syringe, due to the dead air space in the pump. Second, the user does not have the "feel" of suction and therefore may not realize if and when the distal tip of the catheter is clogged. In cases where the catheter does not aspirate the clot but acts as a suction attachment whereby the clot can be pulled back, knowing when the catheter "loses" vacuum can be critical. Some users will gently move the catheter forward to re-engage the clot with the suction at the tip of the catheter when they feel this loss. This feature is not so important when the pump is used with systems that break up a clot, as in this case all the clot is aspirated through the lumen of the catheter. However, there is clinical benefit to being able to remove the clot in one piece, or in as large a section as possible due to the fact that there is less potential for pieces of clot to break off and flow distally into the brain.

A disadvantage of all current aspiration devices is the standard connection to the catheter. Standard catheters have a female Luer connector on the proximal end of the catheter. Any device connecting to the female Luer connector has a male Luer connector. This type of connection creates a flow restriction and a step inside the Luer connection, which may cause a clot or a portion of a clot to catch on the step, especially in cases where a large volume clot is being aspirated in one piece. Not only does this interfere with aspiration, but there is risk that the clot caught in the connector would be flushed back into the brain when the user flushes contrast or other solution through the catheter.

SUMMARY

Disclosed is an aspiration device that can be used to aspirate an obstruction from a blood vessel. The disclosed aspiration device is configured to allow controlled one-handed aspiration yet maintain a syringe plunger "feel" of vacuum. The aspiration device also allows one-handed injection to empty the device when needed. Also disclosed are mechanisms that enable one-handed locking of a plunger position of the device to maintain vacuum when the user releases the device. Also disclosed are connectors that eliminate a flow restriction or step when a device is attached to a catheter. This permits an optimization of aspiration of clot from the catheter and all connections. Also disclosed are valve configurations that facilitate emptying the aspiration device in cases where the aspiration device is filled but further aspiration is desired. Embodiments that combine these features are also disclosed.

In one aspect, there is disclosed a device for aspirating fluid from a body lumen, comprising: a chamber configured to contain fluid, the chamber having an opening through which fluid can be injected out of the chamber and through which fluid can be aspirated into the chamber; a plunger having a plunger seal movably positioned inside the chamber; first and second finger elements coupled to the chamber and the plunger, wherein movement of the first and second finger elements toward one another causes relative movement between the plunger seal and the chamber so as to aspirate fluid into the chamber; and a locking mechanism movable between a first state and a second state, wherein the locking mechanism locks a position of the plunger seal relative to chamber when the locking mechanism is in the first state, and the locking mechanism permits relative movement of the plunger seal relative to chamber when the locking mechanism is in the second state.

In another aspect, there is disclosed an adapter for connecting a female luer connector to an aspiration device, the adapter comprising: a structure having a first end with an opening configured to receive the female Luer connector and a second end with an opening configured to receive an end of the aspiration device; the structure having an internal contour sized and shaped to provide a smooth transition between the end of the aspiration device and the end of the female Luer connector such that the adapter forms an internal lumen connection between the aspiration device and the female Luer connector that lacks any ledges.

In another aspect, there is disclosed a stopcock valve adapted to connect an aspiration device to a catheter, the valve comprising: a first port configured to couple to an aspiration device; a second port configured to couple to a catheter; a third port configured to couple to a receptacle; and an actuator that can be actuated to control fluid flow between the first port and one of the second and third ports, wherein, when the actuator is in a default state, fluid flow is open between the first port and only the second port, and when the actuator is actuated, fluid flow is open between the first port and only the third port; and a spring mechanism that biases the actuator toward the default state.

In another aspect, there is disclosed shut off valve that controls flow of fluid between a catheter and aspiration device, the shut off valve comprising: a structure having a first portion that attaches to a catheter and a second portion that attaches to an aspiration device; a seal inside the structure, the seal having an internal lumen that provides a fluid passageway between the catheter and the aspiration device, wherein the seal is made of a resilient material that can be compressed so as to close the internal lumen and inhibit fluid flow between the catheter and aspiration device; and an actuator that can be actuated to compress the seal.

In another aspect, there is disclosed a device for aspirating fluid from a body lumen, comprising: a chamber configured to contain fluid, the chamber having an opening through which fluid can be injected out of the chamber and through which fluid can be aspirated into the chamber; and a vacuum indicator system coupled to the chamber, the vacuum indicator system having a display that provides an indication as to a level of vacuum inside the chamber.

Other features and advantages should be apparent from the following description of various embodiments, which illustrate, by way of example, the principles of the disclosure.

BRIEF DESCRIPTION OF THE DRAWINGS

FIGS. 12 and 13 each show side and cross-sectional views of the syringe handle.

FIG. 23 shows the hub with a valve in a closed state and FIG. 24 shows it in an open state.

FIG. 25 shows a device with a valve in a closed state. FIG. 26 shows the device with a valve in an open state.

DETAILED DESCRIPTION

Disclosed is an aspiration device that can be used to aspirate an obstruction from a blood vessel. The disclosed aspiration device is configured to allow controlled one-handed aspiration yet maintain a syringe plunger "feel" of vacuum. The aspiration device also allows one-handed injection to empty the device when needed. Also disclosed are mechanisms that enable one-handed locking of a plunger position of the device to maintain vacuum when the user releases the device. Also disclosed are connectors that eliminate a flow restriction or step when a device is attached to a catheter. This permits an optimization of aspiration of a clot or occlusion from the catheter and all connections. Also disclosed are valve configurations that facilitate emptying the aspiration device in cases where the aspiration device is filled but further aspiration is desired. Embodiments that combine these features are also disclosed.

Syringe-Type Aspiration Devices

There exist current syringe-type devices that are configured to facilitate one-handed aspiration by a user squeezing portions of the device towards one another, rather than separating the syringe plunger and barrel as with a traditional syringe. However these types of devices lose aspiration force when the grip on the device is relaxed or released. Disclosed is a one-handed aspiration device having a latching feature, such as a latch, detent, or other locking mechanism, that enables locking the plunger in place, thus giving the user the ability to maintain vacuum force even when the user's grip is relaxed or released from the device, i.e. a vacuum lock.

Figure 1:
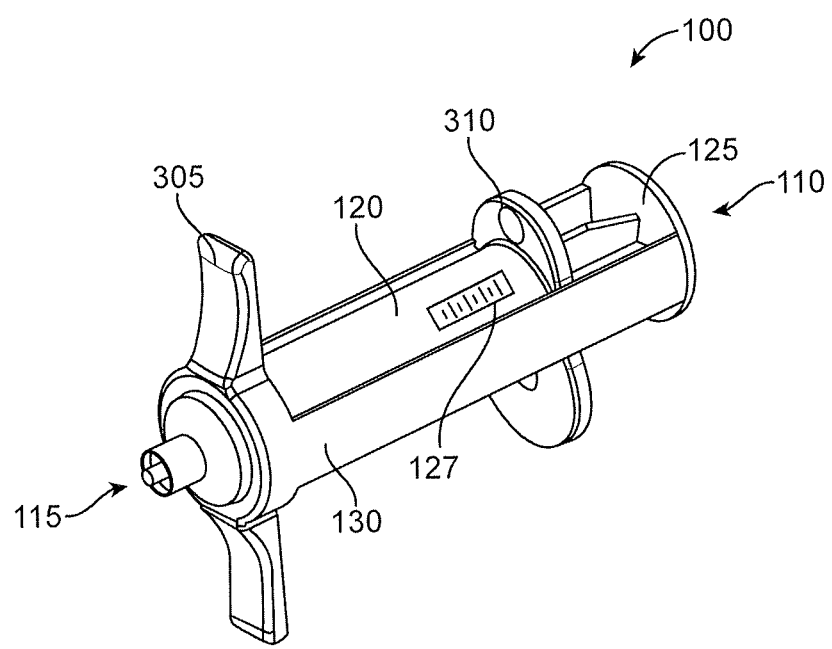
FIG. 1 shows an example of a syringe device configured for one handed aspiration.

FIG. 1 shows an example of a syringe device 100 configured for one-handed aspiration. The syringe device 100 has a distal end 110 through which a fluid is injected or aspirated, and a proximal end 115. The syringe 100 includes a main syringe barrel 120 that defines a chamber that can contain a fluid. A syringe plunger 125 is sized and shaped to slide within the barrel 120 so as to push fluid out of the barrel or pull fluid into the barrel in a well-known manner. An outer syringe barrel 130 is attached to the syringe plunger 125 such as via adhesive, snap fit, screws, etc. The syringe plunger 125 and outer syringe barrel 130 collectively form a body that is slideably coupled to the main syringe barrel 120 such that they can slide relative to the main syringe barrel 120 with a portion of the plunger 125 sliding through the chamber in a proximal or distal direction.

Figure 2:
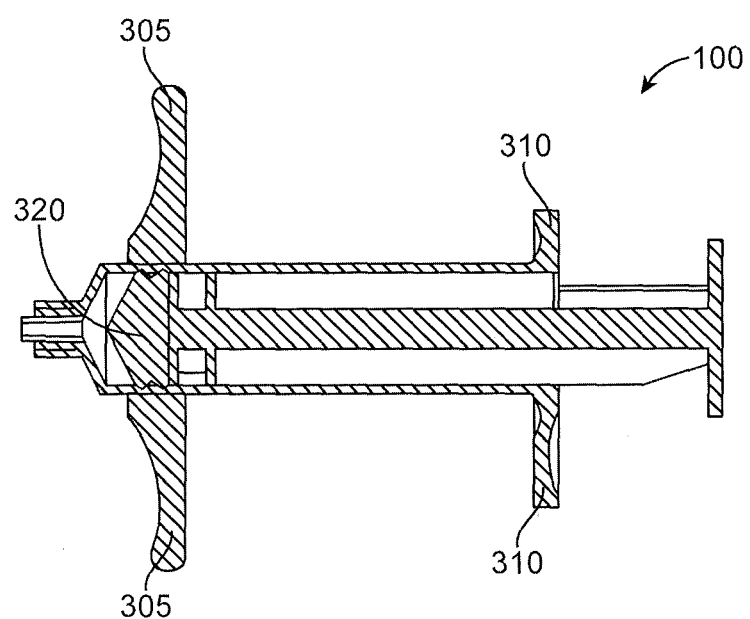
FIG. 2 shows side and cross-sectional views of the syringe.
Figure 3:
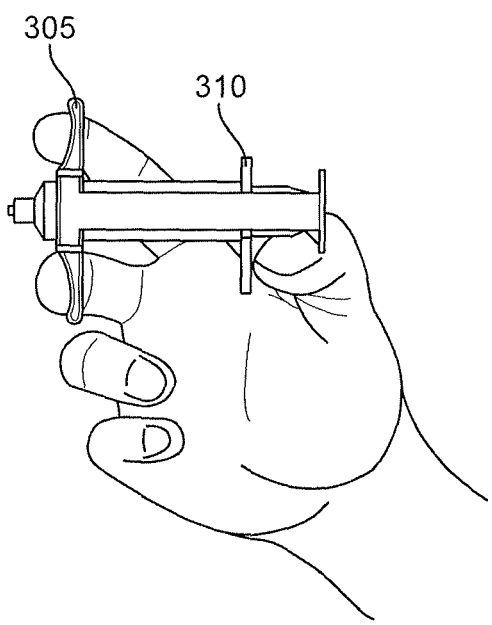
FIGS. 3 and 4 shows the syringe in use.

FIG. 2 shows side and cross-sectional views of the syringe 100. The syringe 100 includes a syringe plunger seal 320 attached to the end of the syringe plunger 125 to seal the fluid in the main barrel. The syringe 100 also includes one or more tabs 305 that are attached to a distal region of the outer syringe barrel 130. One or more tabs 310 are attached to a proximal region of the main syringe barrel 120 at a location proximal of the tabs 305. To aspirate fluid into the chamber, a user positions his or her fingers on a distal side of the tabs 305 such as with the index and middle fingers. The user also positions the thumb on a proximal side of the main syringe barrel tab 310, as shown in FIG. 3. The index/middle fingers and thumb are then squeezed together to move the tabs 305 and 310 toward one another, which causes the plunger 125 to move in a proximal direction relative to the inside of the main barrel chamber. That is, the movement of the outer syringe barrel 305 proximally will likewise move the syringe plunger 125 proximally (relative to the inside of the chamber) to create an aspiration force in the barrel chamber. In an embodiment, there is a vacuum lock consisting of a latching mechanism that can fix the outer syringe barrel 130 to the main syringe barrel 120 such that when the latch is actuated, aspiration force is maintained even if force on the finger tabs 305 and 310 are relaxed or released. A latching mechanism may comprise a feature on the outer syringe barrel that when toggled inward engages with a feature on the main syringe barrel to lock the two components together.

Figure 4:
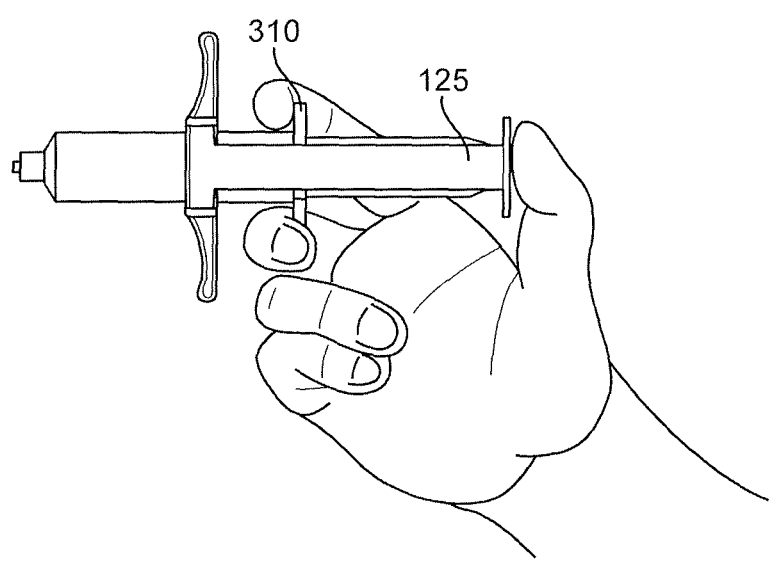

To inject or expel fluid from the barrel chamber, the user places the index and middle fingers on a distal side of the main syringe barrel finger tabs 310 and the thumb on a proximal or proximal-most side the plunger 125 (or on a corresponding tab attached to the plunger 125), as shown in FIG. 4. The index/middle fingers and thumb are then squeezed together as described above. This causes the plunger 125 to move in a distal direction relative to the inside of the main barrel chamber and expel any fluid distally out of the chamber.

One advantage of the above-described configuration over some other syringe handle configurations is that the sizes of the syringe 100 need not be much bigger than the size of a standard syringe of comparable volume. Another advantage of the syringe 100 is that the user's hand is set closer to or essentially over the body of the syringe, which allows good control/stabilization of the syringe as compared to some other aspiration devices.

Figure 5:
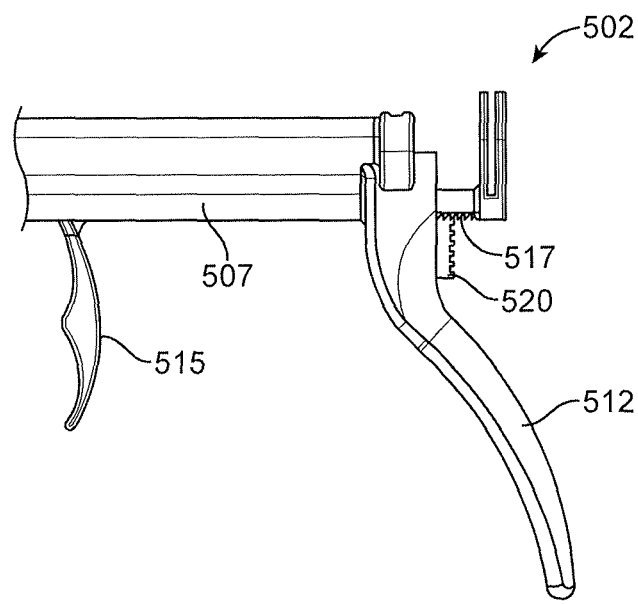
FIG. 5 shows embodiment of a syringe handle in an assembled state.
Figure 6:
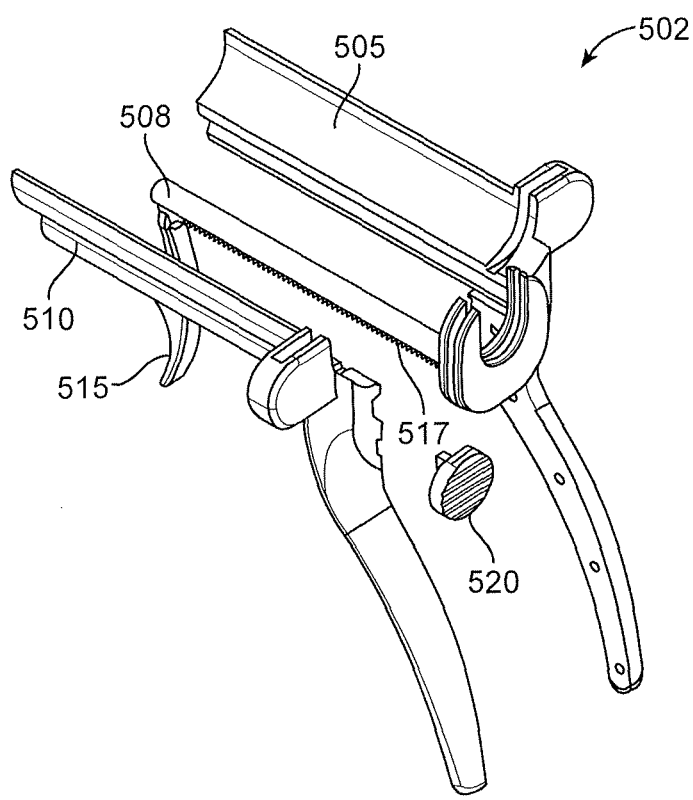
FIG. 6 shows the syringe handle in an exploded state.
Figure 7:
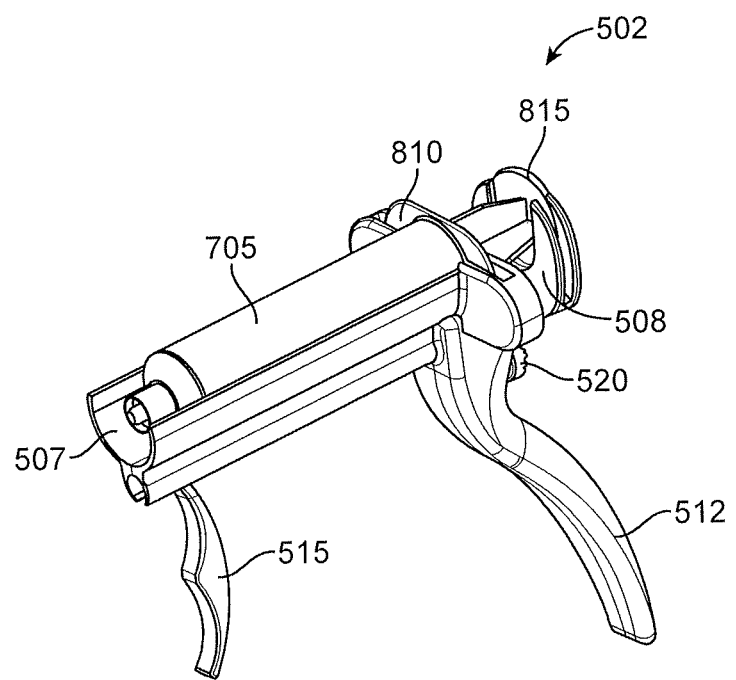
FIG. 7 shows a standard syringe attached to the syringe handle.

Another example of a one-handed manual aspiration device is a pistol grip style design; examples are disclosed in U.S. Pat. No. 4,594,073, U.S. Pat. No. 5,115,816, U.S. Pat. No. 5,469,860, and U.S. Pat. No. 5,830,152, all of which are incorporated herein by reference. In an embodiment, a pistol-grip style syringe aspiration device includes a latch mechanism to lock the plunger with respect to the main syringe barrel to create a vacuum lock. FIG. 5 shows embodiment of a syringe handle 502 in an assembled state and FIG. 6 shows the syringe handle 502 in an exploded state. The syringe handle 502 has a main handle body formed of a right main handle body 505 and a left main handle body 510 that collectively form a syringe barrel holder 507 that can receive a standard syringe 705 (as shown in FIG. 7). A slide piece 508 is slideably coupled to the syringe barrel holder 507 when the right main handle body 505 and left main handle body 510 are joined together. With reference still to FIGS. 5 and 6, a finger grip 515 is coupled to the slide piece 508 and a palm grip 512 is attached to the syringe barrel holder 507. A finger toggle 520 is moveably attached to the syringe barrel holder 507 and configured to be moved upward or downward relative to a set of teeth or ratchets 517 on the slide piece 508, such that the finger toggle 520 engages or disengages the teeth to lock the slide piece with respect to the syringe barrel holder 507.

With reference to FIG. 7, a standard syringe 705 can be attached to the syringe handle 502 by pressing the syringe 705 into the barrel of the syringe handle 502, with a flange 810 of the syringe 705 sliding into a slot of the main handle body 510, and a proximal tab 815 of a plunger of the syringe 705 sliding into a proximal slot of the slide piece 508. In this manner, the barrel of the syringe is fixed to the syringe barrel holder 507 and the syringe plunger is fixed to the slide piece 508. In another embodiment, the syringe 705 may be integrated into the syringe handle 502 as a monolithic structure.

To pull vacuum/aspirate fluid into the syringe 705, the toggle 520 is set to the downward (disengaged) position, and the user holds the syringe handle 502 in a manner similar to a pistol with the index and middle fingers on the finger grip 515 and palm around the palm grip 512. The user then squeezes the finger grip 515 towards the palm grip 512 to aspirate. The finger toggle 520 can be engaged with the ratchets 517, by pushing the finger toggle 520 upward, at any time in order to maintain and lock vacuum on the syringe 705 by preventing motion of the syringe plunger with respect to the barrel.

Figure 8B:
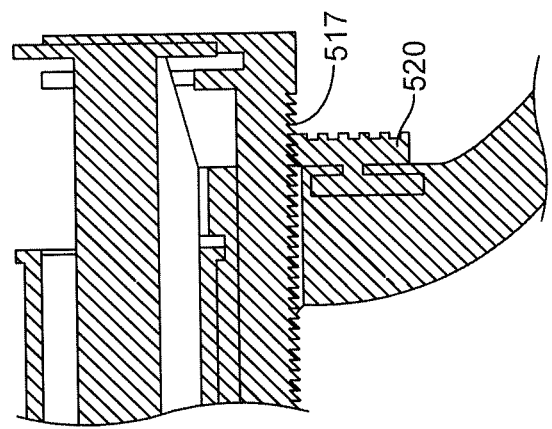
FIGS. 8A and 8B show a finger toggle of the device in two positions.
Figure 8A:
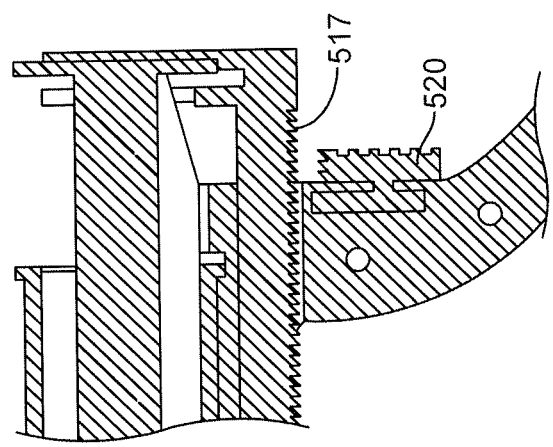

FIGS. 8A and 8B show the finger toggle 520 in two positions: an unlocked position (FIG. 8A) where the finger toggle 520 does not engage the ratchets 517, and a locked position (FIG. 8B) where the finger toggle 520 engages the ratchets 517 (thereby limiting movement). The toggle may be configured with a snap feature such that the up and down positions are two stable positions of the toggle. For example, there may be a movable projection on one side and two detents on the other corresponding to the two positions. To inject fluid out of the syringe chamber, the user moves his or her hand to the main body handle, with the thumb placed on the back (proximal) side of the syringe plunger and pushes the thumb forward (distal) to move the plunger of the syringe in a distal direction through the chamber of the syringe.

Figure 9:
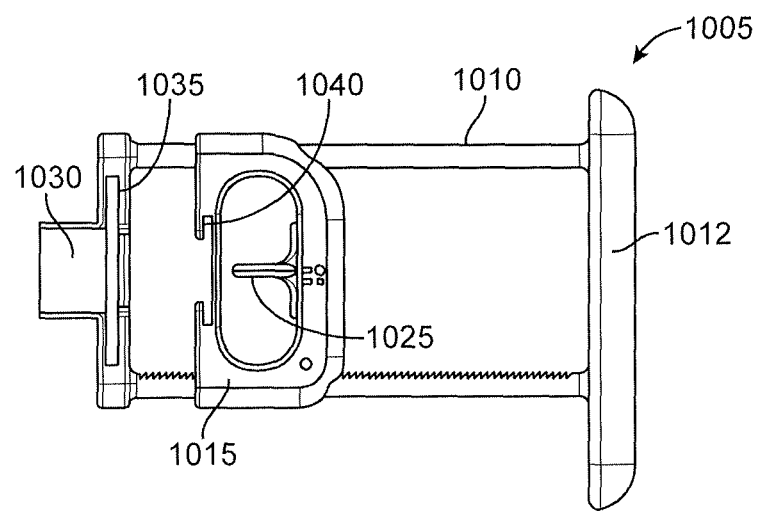
FIGS. 9 and 10 show an embodiment of a syringe handle.
Figure 10:
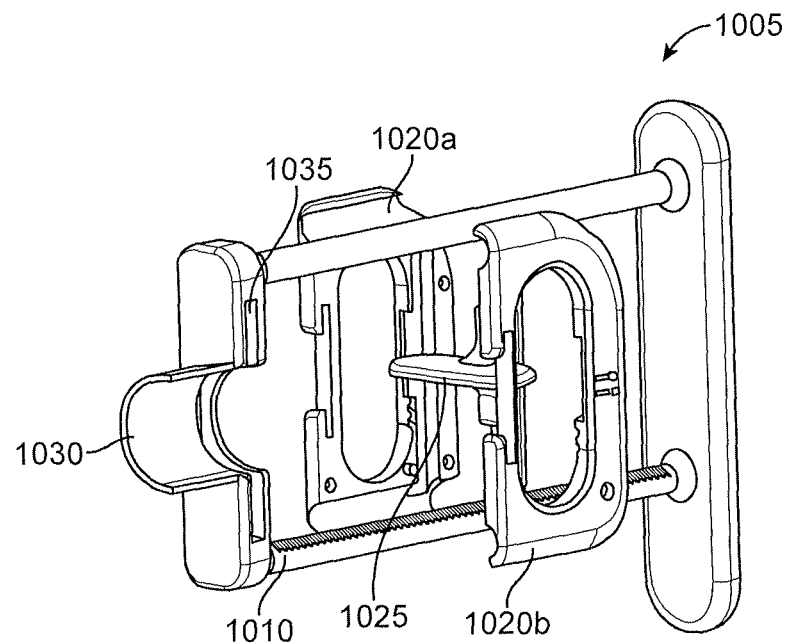

The vacuum lock concept may be applied to other aspiration syringe handle designs, for example those disclosed in U.S. Pat. No. 3,819,091, U.S. Pat. No. 4,711,250, and U.S. Pat. No. 4,850,979. An embodiment 1005 is shown in FIG. 9. FIG. 10 shows the syringe handle 1005 in an exploded state. As best shown in FIG. 10, the syringe handle 1005 is made up of at least four components (although the quantity of components may vary) including a main handle 1010 with a proximal palm grip 1012, a left finger grip 1020a, a right finger grip 1020b, and a finger toggle 1025. The components attach to one another to collectively form the assembled syringe handle 1005. The left and right finger grips 1020a and 1020b are assembled to form the slideable finger grip 1015. When assembled, the slideable finger grip 1015 captures the finger toggle 1025 and is slideably coupled to the main handle 1010.

Figure 11:
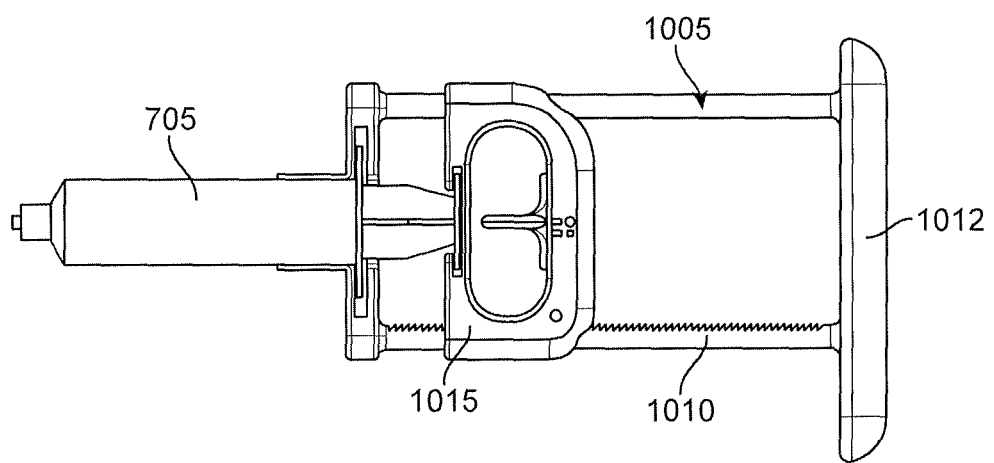
FIG. 11 shows a standard syringe attached to the syringe handle.

When assembled, a standard syringe 705 can be attached to the syringe handle 1005 by pressing the barrel portion of the standard syringe into a distal seat 1030 of the main handle 1010 with a flange of the syringe body sliding into a slot 1035 of the main handle 1010. The proximal tab of the standard syringe plunger slides into a slot 1040 of the finger grip 1015. FIG. 11 shows the standard syringe 705 attached to the syringe handle 1005.

The finger toggle 1025 is configured to fix the position of the finger grip 1015 with respect to the main handle 1010 as shown in FIGS. 12 and 13. In the on position shown in FIG. 12, (which may be noted by a designation such as "O" on the finger grip), a set of internal teeth 1305 of the finger toggle are disengaged from corresponding teeth 1310 of the main body. The finger grip is thus free to move thereby allowing the user to retract (pull vacuum) and advance (inject) the plunger on the standard syringe by sliding the finger grip proximally or distally. In the off position shown in FIG. 13 (which may be noted by a designation such as "X" on the finger grip), the internal teeth 1305 of the finger toggle engage the teeth 1310. This allows the user to lock the syringe plunger in place, as is necessary to maintain and lock the vacuum.

To aspirate into the device 1005 or to create an aspiration force, the user places the index and middle fingers through the finger grip 1015 and secures the palm grip 1012 in his palm. The user then verifies that the finger toggle 1025 is in the on or "O" position. Using these two fingers, the user then pulls the finger grip towards the palm grip 1012 of the main handle 1010. If desired, the user may then lock the syringe plunger in place (so as to maintain vacuum) by switching the finger toggle 1025 to the "X" position using a finger such as the forefinger. The opposite motion on the finger toggle 1025 using a finger such as the middle finger will disengage the lock. As above, the toggle may be configured to have two stable positions.

To inject fluid from the device, the user then moves the index and middle fingers to the distal portion of the syringe main handle 1010, with the thumb placed in the finger grip hole or on the back (proximal) side of the finger grip 1015, and squeezes the finger grip 1015 and palm grip 1012 of the main handle 1010 together.

Figure 14:
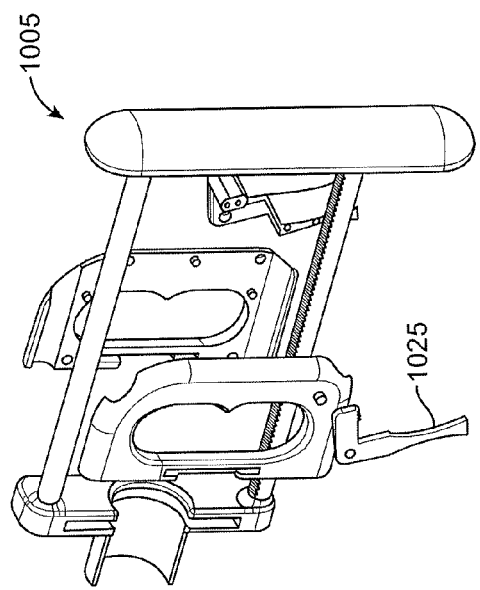
FIG. 14 shows another embodiment of a syringe handle.
Figure 15A:
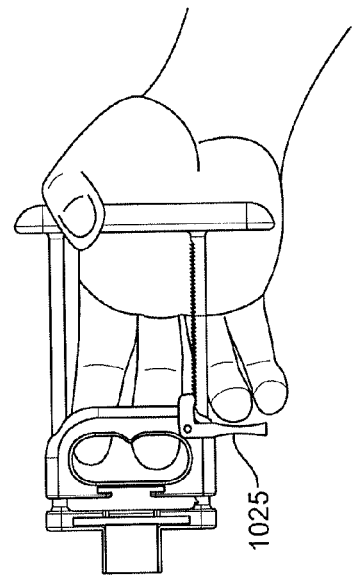
FIGS. 15A and 15B show the syringe handle in use.
Figure 15B:
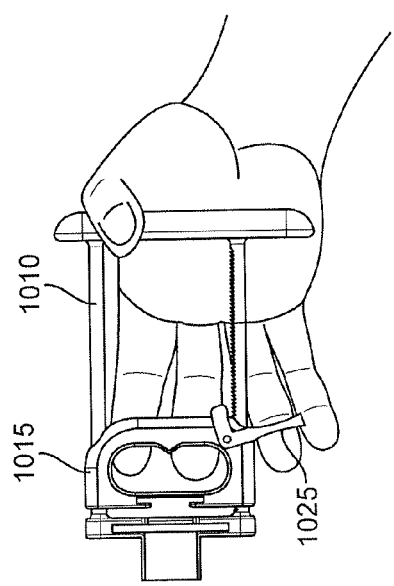

In another embodiment of the syringe handle 1005 shown in FIG. 14, the finger toggle 1025 is positioned outside of the finger grip 1015. The finger toggle 1025 is positioned such that the actuation of the locking mechanism of the finger toggle 1025 can be ergonomically performed using the ring finger. The finger toggle 1025 is pulled back to disengage the teeth on the main handle (as shown in FIG. 15A) and pushed forward to engage the teeth on the main handle lock the syringe plunger in place (as shown in FIG. 15*b*).

During use, it is often valuable for the user to note the level of vacuum in the aspiration device. For example, a loss of vacuum force indicates either that the blood vessel occlusion is being suctioned or has been suctioned into the catheter, or that the catheter tip has lost engagement with the occlusion. In addition, it may be important to know if the vacuum is too high. In some cases a vacuum that is too high may cause damage to the catheter and/or to the vessel wall, for example causing the catheter to collapse. In an embodiment of the aspiration device, the device includes an indicator 127 (FIG. 1) which shows the level of vacuum in the main chamber of the aspiration device. This indicator may provide or otherwise indicate a pressure value, for example in mmHg. Alternately, the indicator may show or otherwise represent a pressure level and include markings to show when the level is above or below a target level. In this way, the user can visualize if the level of vacuum is being maintained or going down or is changing. In an embodiment, the vacuum indicator is a simple piston on a spring that is fluidly connected to the vacuum chamber, wherein the piston position varies depending on the amount of vacuum. Alternately, the vacuum indicator is a flexible bellow that has an inherent spring constant or which is connected to an external spring, and which shortens with increased level of vacuum. Markings on the housing may identify the length of the flexible bellows and relate this to the level of vacuum.

In another embodiment, the aspiration device has a feature that maintains a constant level of vacuum. For example the piston generating the vacuum is coupled to a spring such that the pull-back force is constant. In a variation of this embodiment, the user can switch between manually controlling the vacuum force and switching to automated vacuum, for example with a switch that can engage or disengage the spring that generates the vacuum. This embodiment may also be used with or without the vacuum indicator described above. In this version, the pull back mechanism may be coupled to the vacuum indicator to allow for a constant vacuum. For example, the vacuum indicator is an electronic vacuum sensor, which imparts a signal to a solenoid actuated piston that generates the aspiration force.

Connectors

Figure 16:
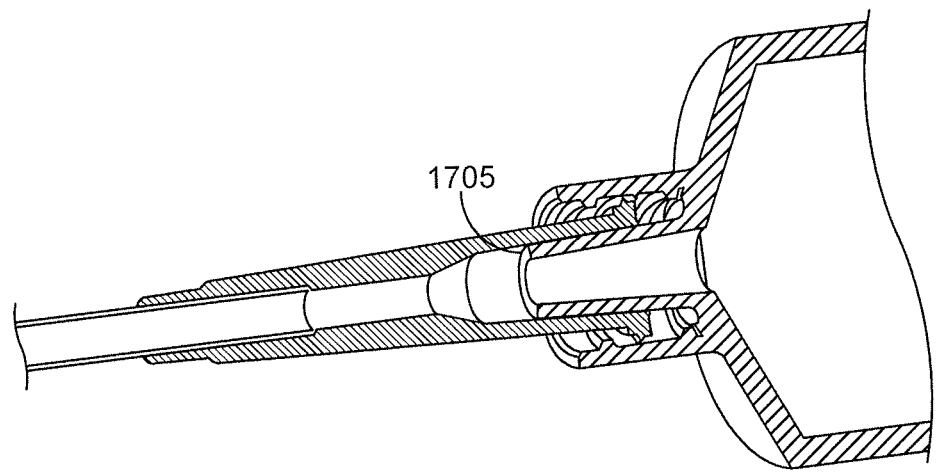
FIG. 16 shows a cross-sectional view of a conventional male Luer connector on the distal tip of a syringe coupled to a female Luer connector on the proximal end of a catheter.

Connections to catheters have been standardized to a locking Luer taper design, with a male Luer taper connecting to a female Luer receptacle. The tapered connection provides a fluid-tight seal. Usually the male Luer connector has external threads and the female Luer connector has external features which can engage the threads when the connection is made, enabling the connection to be able to withstand pressure without the two sides of the connector coming apart. Typically catheter proximal hubs have a female Luer design. Syringes, stopcocks, Rotating Hemostasis Valves (RHVs), or other devices designed to connect to catheters have a male Luer design. FIG. 16 shows a cross-sectional view of a conventional male Luer connector on the distal tip of a syringe coupled to a female Luer connector on the proximal end of a catheter. When coupled, a distal end of the male Luer taper creates a ledge 1705 at the interface between the male and female connectors. During aspiration of clot through the catheter, the clot to may get caught or hung up on the ledge 1705. The ledge 1705 also reduces the cross sectional area of the lumen for the clot to flow through.

Figure 17:
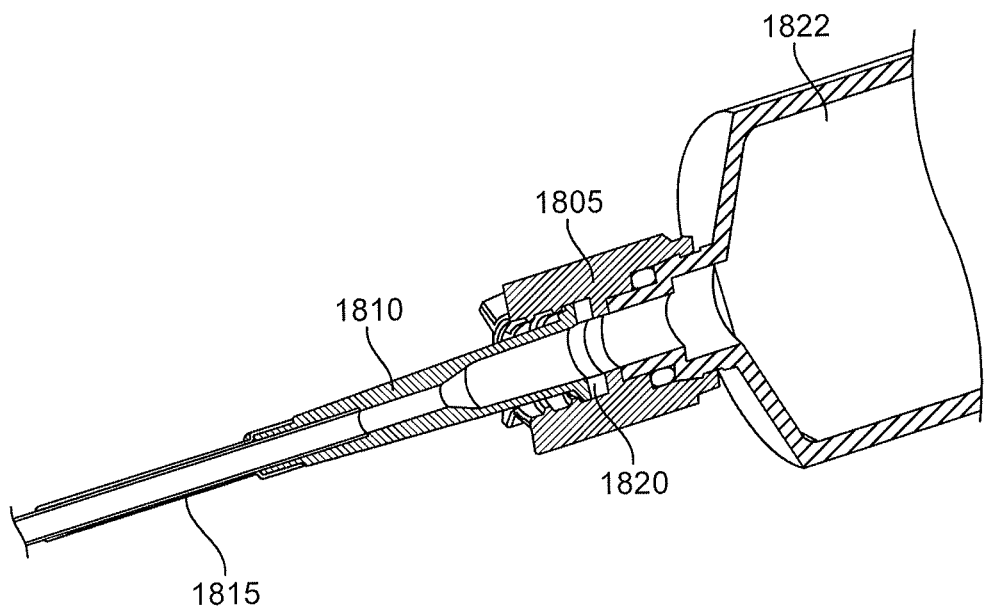
FIG. 17 shows a cross sectioned perspective view of a connector adaptor on the distal tip of an aspiration device coupled to a female Luer connector on the proximal end of a catheter.

There is now described an unrestricted connector adaptor that replaces the male Luer which typically attaches to a female Luer connector on a catheter. FIG. 17 shows a cross sectioned perspective view of a connector adaptor 1805 on the distal tip of an aspiration device 1822, coupled to a female Luer connector 1810 on the proximal end of a catheter 1815. The adaptor 1805 provides a connection to the female Luer connector which eliminates the aforementioned ledge 1705 (FIG. 16). The adaptor 1805 does not contain a taper that fits into the female connector 1810, but instead seals the connection with a gasket 1820 on the top surface (i.e., proximal surface) of the female Luer connector 1810. The adaptor 1805 can spin about a longitudinal axis of the catheter 1815 with respect to the main body of the aspiration device 1822 and contains internal threads 1817. To attach the adaptor 1805 to the catheter, the two sides of the connection are pressed together and the connector 1805 is rotated to secure the internal threads to the external threads of the female Luer 1810 on the catheter such that the gasket 1820 is compressed to provide a fluid tight seal.

Figure 18:
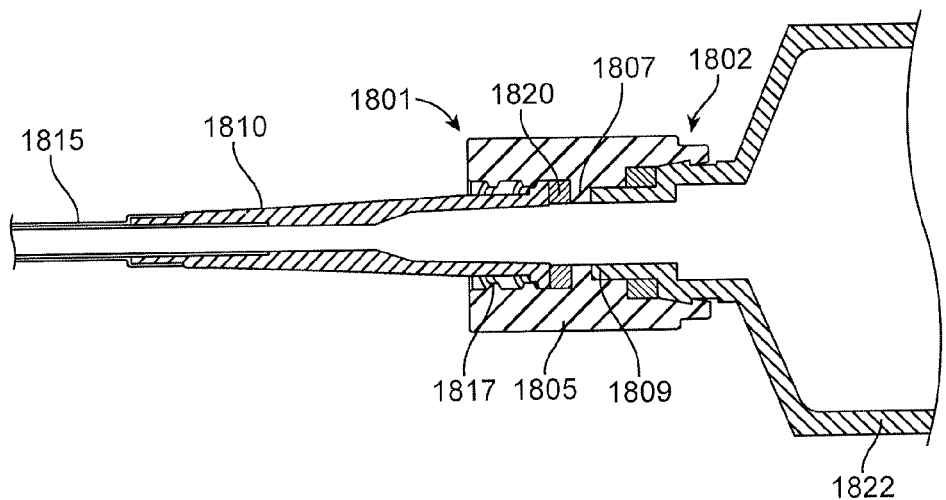
FIG. 18 shows an adapter system in cross-section.

FIG. 18 shows the system in cross-section, with a clearer view of the unrestricted interface between the female Luer hub of the catheter 1815 and the syringe 1822 with the adaptor 1805 providing a connection between the female Luer connector 1810 and the syringe 1822. The adapter 1805 has a first, distal end 1801 with an opening that is configured to receive therein the female Luer connector 1810. The gasket 1820 is positioned inside the opening such that the gasket 1820 abuts and seals against a proximal-most end of the female Luer connector 1810 when the female Luer connector 1810 is mounted inside the opening. The adapter has a proximal end 1802 with an opening that receives therein the distal most end of the syringe 1822 (or other device) through which fluid is aspirated into or injected out of the syringe. An internal contour or structure, such as a protrusion 1807 inside the adapter 1805, links the opening that receives the syringe 1822 to the opening that receives the female Luer connector 1810. The protrusion is sized and shaped to provide a smooth transition between the distal tip 1809 of the syringe 1822 and the proximal tip of the female Luer connector 1810. The gasket 1820 also assists in providing the smooth transition. In this manner, the adapter 1805 provides an internal lumen connection between the syringe 1822 and the female Luer connector 1810 with the internal lumen connection providing a smooth transition that lacks any sudden steps or ledges. In this embodiment, the connector adaptor 1805 can rotate freely with respect to the aspiration device 1822, such that the threads of the female Luer can be engaged without rotating the entire device. The gasket 1820 provides a fluid seal between the adaptor 1805 and the aspiration device 1822 such that there is no internal, stepped ledge in the lumen that connects the syringe 1822 to the catheter 1815.

Figure 19:
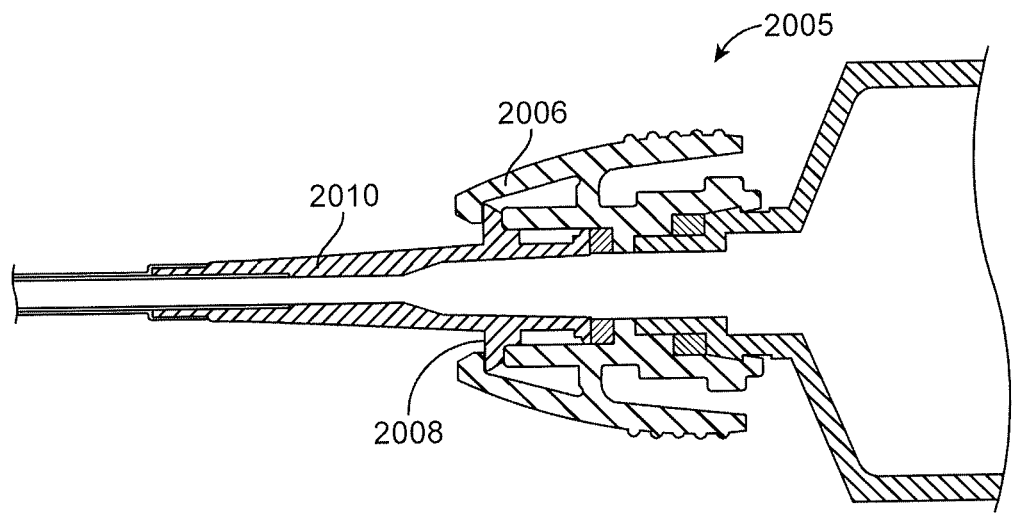
FIG. 19 shows another embodiment of a connector adaptor.

FIG. 19 shows another embodiment of a connector adaptor 2005. This adaptor 2005 includes a clasp structure 2006 that is configured to "snap" on to a portion, such as a flange 2008, of the female connector 2010. A leading edge of the flange 2008 and the clasp structure 2006 form bevels such that pushing the two components together allows the clasp features to automatically open and then snap over the flange 2008. Squeezing on the back end of the clasp structure 2006 lift the front end of the clasp structure away from the flange 2008 and allows uncoupling of the connector.

Valve

In the situations where the clinician has filled the syringe to its maximum capacity, there is a need to expel the contents of the aspiration device, for example a syringe, in order to continue the aspiration thrombectomy. The clinician typically removes the syringe from the catheter in order to expel the contents of the syringe. This creates a loss of vacuum, as well as a risk of introducing air into the catheter as a result of the syringe being removed. If there was a strong vacuum force in the catheter due to clot being trapped in the tip of the catheter, for example, then there is a strong likelihood that removal of the syringe will draw air into the catheter. Alternatively, the clinician may attach a three-way stopcock between the catheter and the syringe or aspiration device, wherein a third port of the stopcock leads to a receptacle to store the aspirant. However, standard three-way stopcocks can at times be confusing as to which ports are open and which port is closed. In addition, standard stopcocks require two hands to open, and two hands to close. Further, the connections to standard stopcocks are Luer connections with their associated restriction and ledge, creating a potential for thrombus or other emboli to be trapped in the valve.

Figure 20:
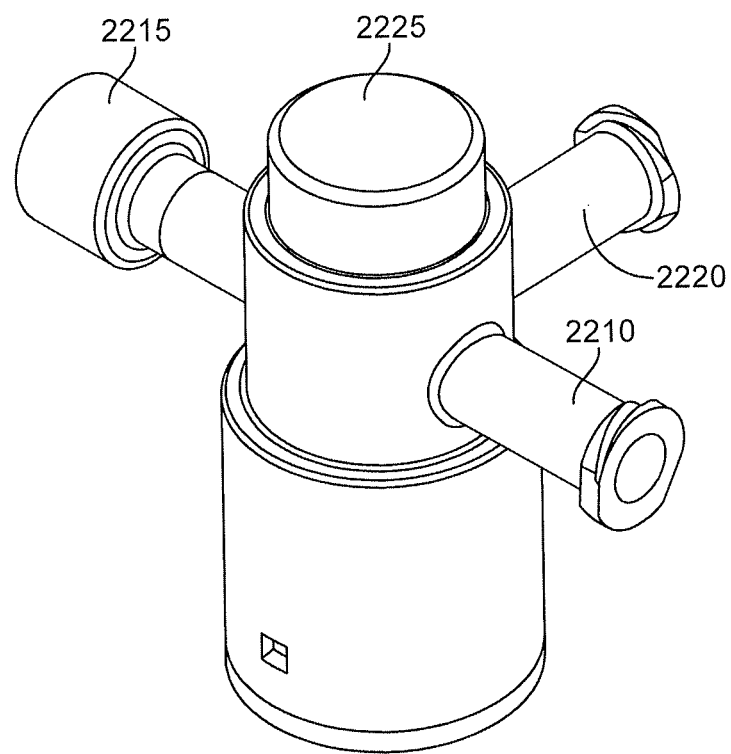
FIG. 20 shows a spring-loaded, push button stopcock.

There is now disclosed a spring-loaded, push button stopcock 2205 as shown in FIG. 20. The stopcock 2205 requires only one hand to open. A user can simply release the stopcock 2205 to close it. The stopcock 2205 includes three ports 2210, 2215, and 2220 and an actuator such as a spring-loaded button 2225.

Figure 21:
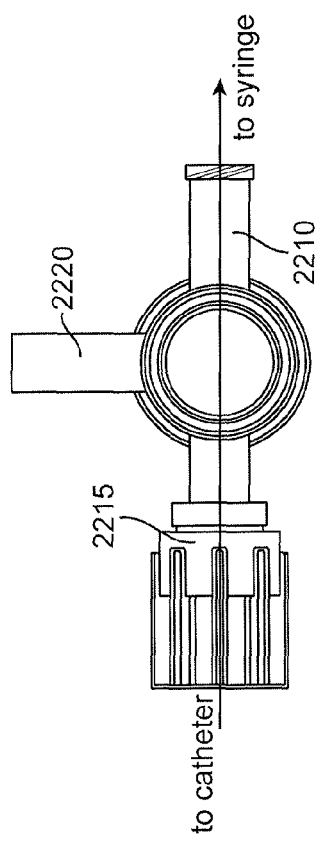
FIG. 21 shows the stopcock configured for direct flow between an attached catheter and a syringe to allow for aspiration.
Figure 21:
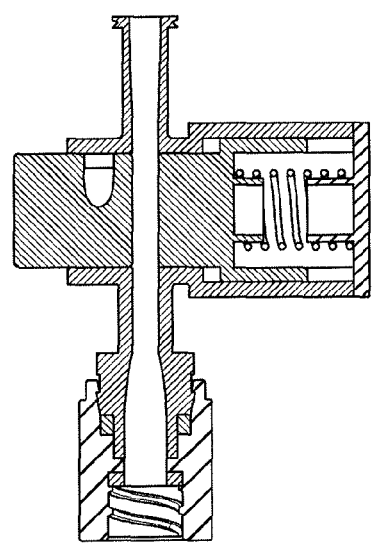
Figure 22:
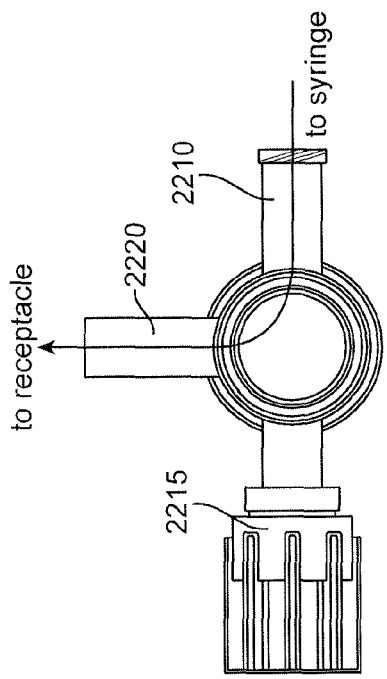
FIG. 22 shows the stopcock configured to allow expulsion from a syringe to an attached receptacle.
Figure 22:
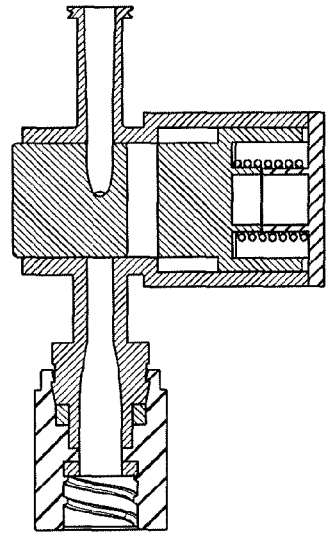

In a default state wherein the button 2225 is not compressed, there is a direct flow between an attached catheter and a syringe to allow for aspiration, as shown in FIG. 21. When the button 2225 is actuated (such as by being compressed), the fluid path changes to allow expulsion from the syringe to an attached receptacle, as shown in FIG. 22. As shown in the embodiment in FIGS. 21 and 22, the valve connections may be configured to be unrestricted.

All the aforementioned valve designs may incorporate the adaptor as described above to minimize the possibility of clot being trapped in the valve during aspiration or emptying of the aspiration device.

Figure 24:
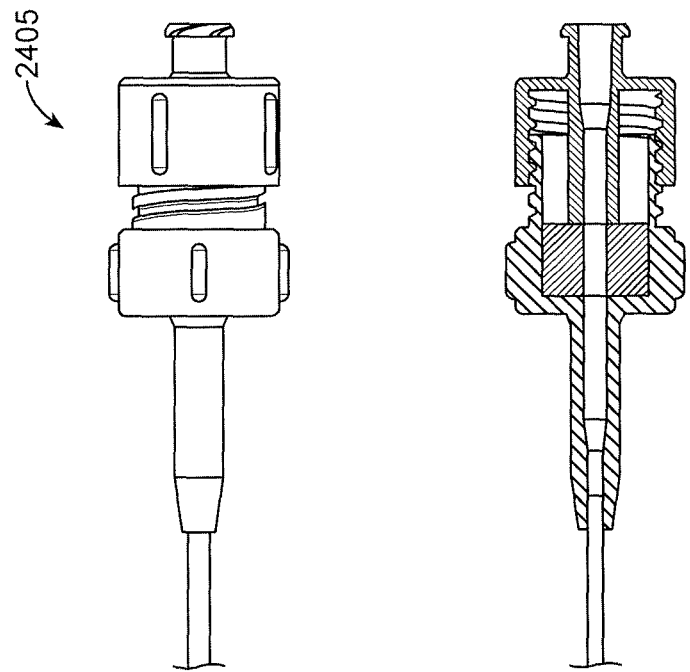
FIGS. 23 and 24 show an embodiment (in side and side cross-sectional views) of a valve built into a catheter proximal hub.
Figure 23:
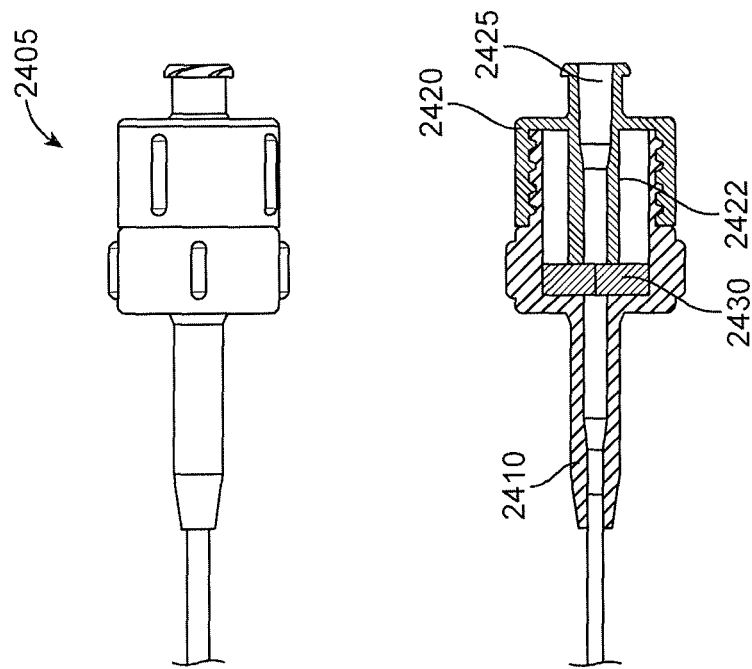

Alternately, the catheter proximal hub may be configured with a shut off valve such that when the aspiration device is removed, the hub automatically closes so that there is no loss of vacuum or possible introduction of air. FIGS. 23 and 24 show one embodiment (in side and side cross-sectional views) of such a valve built into a catheter proximal hub 2405. FIG. 23 shows the hub 2405 with a valve in a closed state and FIG. 24 shows it in an open state. The catheter proximal hub 2405 includes a valve seat 2410, a valve cap 2420 and a valve seal 2430 which is normally closed. The valve seal 2430 may be, for example an elastomeric and/or resilient seal with an inner lumen such as a short length of tube. The valve cap 2420 contains an inner tubular structure 2422 and a proximal female Luer connector 2425. The valve seat 2410 contains external threads and the valve cap contain internal threads such that when the cap is turned, the internal tube is pushed forward to compress the seal 2430 such the inner lumen of the seal is occluded, as in FIG. 23. When the cap is turned in an unscrewing direction, the tube moves back, decompressing the seal 2430 thereby allowing the inner lumen to open, as in FIG. 24. The proximal female Luer connector allows the catheter to be prepped with a standard syringe when the valve is in the open state.

Figure 26:
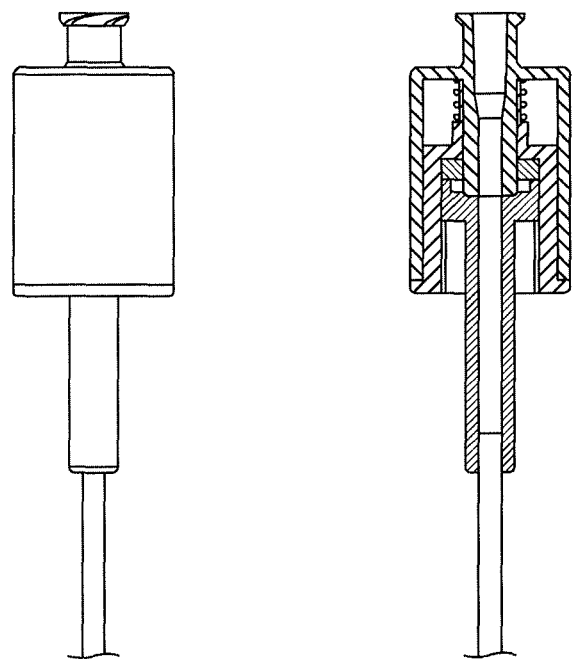
FIGS. 25 and 26 show another embodiment in cross section of a valve built into a catheter proximal hub.
Figure 25:
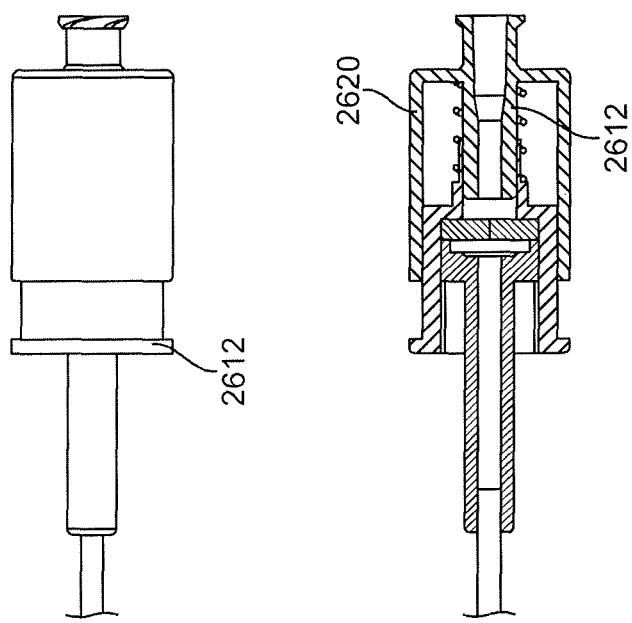

In another embodiment, as shown in FIGS. 25 and 26, the valve seat 2610 and valve cap 2620 are slideably connected to one another. FIG. 25 shows the device with a valve in a closed state and FIG. 26 shows it in an open state. The valve seal 2630 may be, for example, a septum valve with a slit or slits. The valve cap 2620 contains an inner tubular structure 2622 and a proximal female Luer connector 2625. An internal compression spring 2615 biases the valve seat and valve cap to keeps the two components normally apart, as shown in FIG. 25. When the cap is pushed forward, the internal tube 2622 is pushed forward through the valve seal 2630 to open the valve, as shown in FIG. 26. A latch between the valve seat and the valve cap may keep the valve in the opened configuration. However, before the user disconnects the syringe or other aspiration device, the user releases the latch and the compression spring 2615 pulls the internal tube 2622 away from the valve 2630 and allows the valve to close, as in FIG. 25.

Figure 27A:
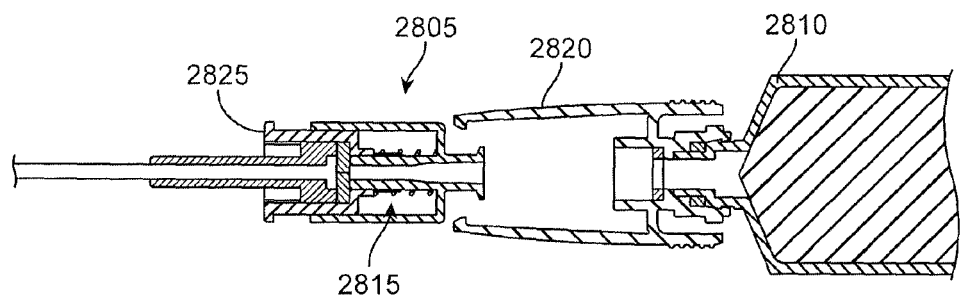
FIGS. 27A-27C show a catheter hub that includes a shut-off valve configured to be connected to an aspiration device
Figure 27B:
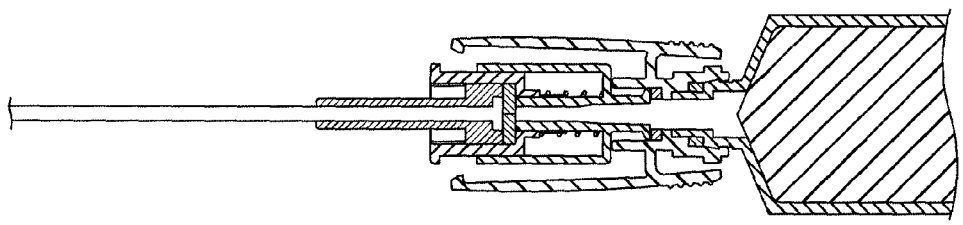
Figure 27C:
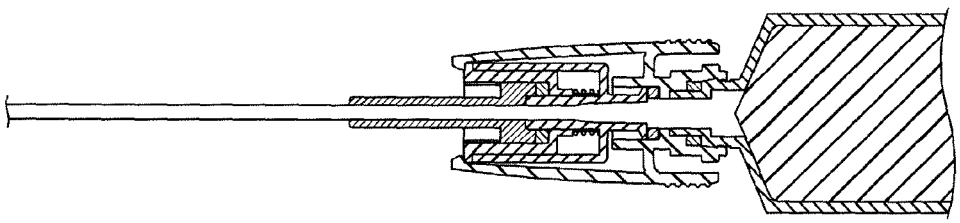

There may be embodiments of aspiration devices and catheters connections that combine several of the features disclosed herein. For example, in FIGS. 27A, 27B, and 27C, a catheter hub 2805 includes a shut-off valve 2815 configured to be connected to an aspiration device 2810 via an unrestricted connector. The connector may contain a latch structure 2820 that locks the aspiration device 2810 to a flange structure 2825 of the hub 2805. When the aspiration device 2810 is pushed forward onto the catheter hub 2805, an unrestricted connection is formed between the aspiration device 2810 and the catheter hub 2805 and simultaneously the valve 2815 is opened to create a smooth and unrestricted lumen from the body of the catheter into the aspiration device. When the aspiration device 2810 is removed, a spring in the shut off valve 2815 prevents loss of vacuum in the catheter.

Figure 28:
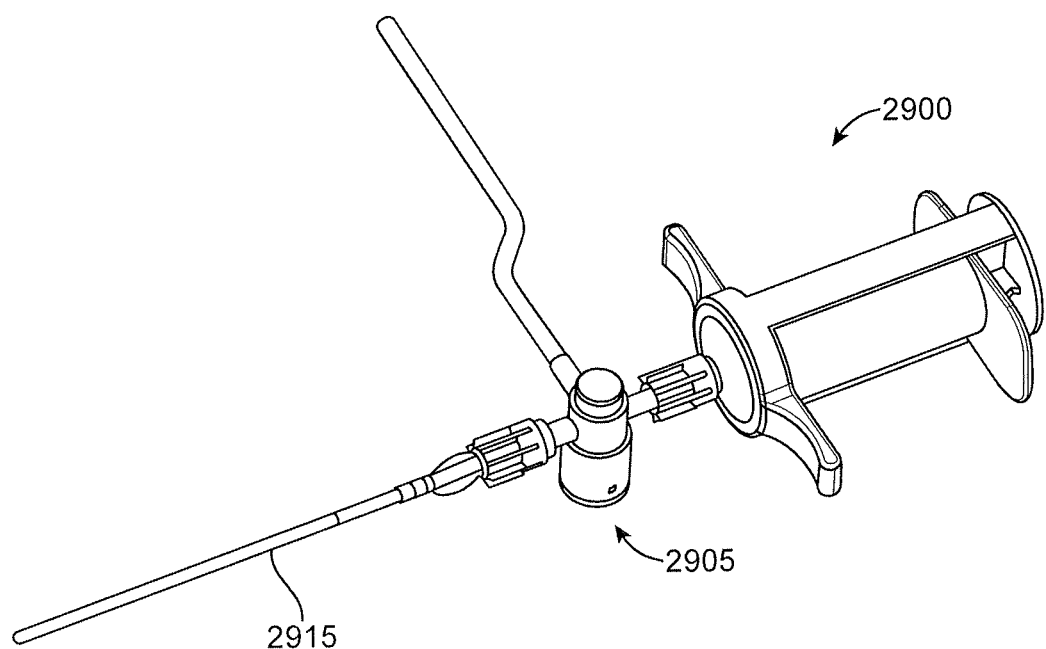
FIG. 28 shows the aspiration device connected using an unrestricted connector design via a push button valve to catheter.
Figure 29A:
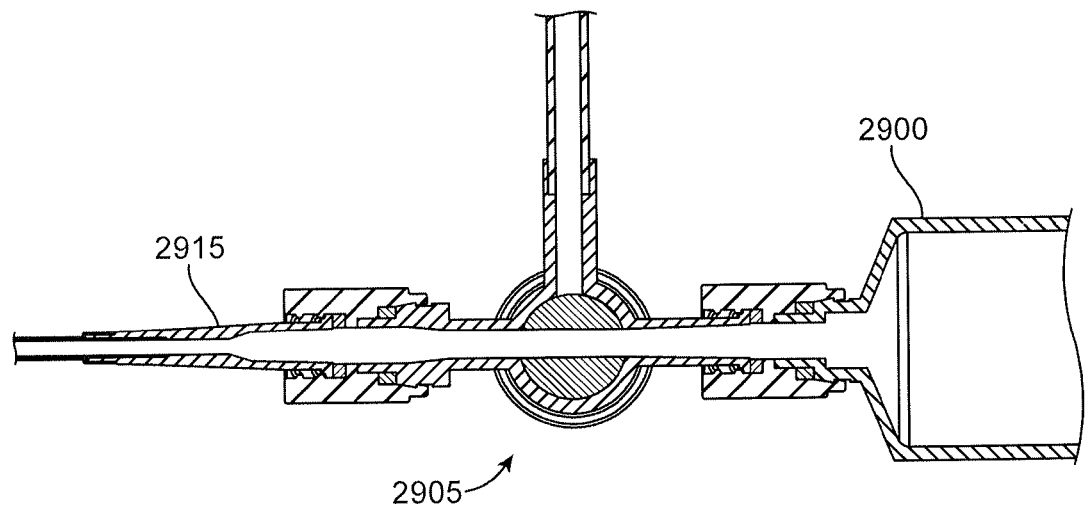
FIGS. 29A and 29B show a cross section of an aspiration device connected using an unrestricted connector design via a push button valve to catheter, with the push button valve in two different states.
Figure 29B:
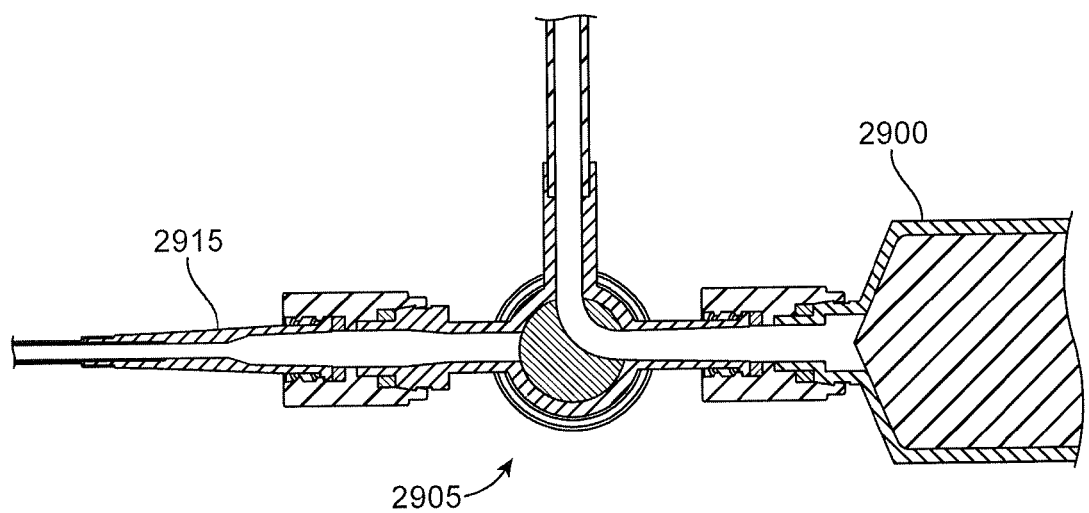

In another embodiment, as shown in FIG. 28, the aspiration device 2900 is connected using an unrestricted connector design via a push button valve 2905 to the catheter 2915. This allows unrestricted aspiration through the catheter when the valve is in the aspiration state, as in FIG. 29A, and allows unrestricted purging of the aspiration device 2900 when the valve 2905 is in a purge configuration, as in FIG. 29B. The valve 2905 may be monolithic with the aspiration device such that the components and connections are minimized. As shown, the aspiration device is configured to be optimized for one-handed aspiration.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A device for aspirating fluid from a body lumen, comprising:
    a cylindrical internal syringe barrel member that defines a chamber configured to contain fluid, the chamber having an opening through which fluid can be injected out of the chamber and through which fluid can be aspirated into the chamber;
    a plunger having a plunger seal movably positioned inside the chamber of the internal syringe barrel;
    a cylindrical external syringe barrel connected to the plunger, wherein the internal syringe barrel is slidably positioned inside the external syringe barrel such that the plunger and the external syringe barrel collectively form a body that is slidably coupled to the internal syringe barrel such that such that the body can slide relative to the internal syringe barrel with the plunger seal sliding through the chamber in a proximal or distal direction;
    first and second finger elements connected to and extending outward from the internal syringe barrel at a proximal end of the internal syringe barrel;
    third and fourth finger elements connected to and extending outward from the external syringe barrel at a distal end of the external syringe barrel;
    wherein movement of the first and second finger elements toward the third and fourth finger elements causes relative movement between the plunger seal within the chamber so as to aspirate fluid into the chamber;
    a locking mechanism movable between a first state and a second state, wherein the locking mechanism locks a position of the plunger seal relative to chamber when the locking mechanism is in the first state, and the locking mechanism permits relative movement of the plunger seal relative to chamber when the locking mechanism is in the second state.

2. A device as in claim 1, wherein at least some of the finger elements are tabs.

3. A device as in claim 1, wherein the locking mechanism is positioned such that a user can use a thumb to change the state of the locking mechanism when the pistol grip is in the hand of the user.

4. A device as in claim 1, wherein the locking mechanism comprises a latch.

5. A device as in claim 1, further comprising:
    A connector structure having a first end with an opening configured to receive a female Luer connector and a second end with an opening configured to receive an end of the external syringe barrel;
    the connector structure having an internal contour sized and shaped to provide a smooth transition between the end of the external syringe barrel and the end of the female Luer connector such that the adapter forms an internal lumen connection between the chamber of the internal syringe barrel and the female Luer connector that lacks any ledges.

6. A device as in claim 5, further comprising a gasket inside the structure, the gasket configured to seal against the female Luer connector.

* * * * *